(12) United States Patent
Joseph (10) Patent No.: US 11,241,275 B2
(45) Date of Patent: Feb. 8, 2022

(54) ENERGY-BASED SURGICAL INSTRUMENT HAVING MULTIPLE OPERATIONAL CONFIGURATIONS

(71) Applicant: COVIDIEN LP, Mansfield, MA (US)

(72) Inventor: Daniel A. Joseph, Golden, CO (US)

(73) Assignee: Covidien LP, Mansfield, MA (US)

( * ) Notice: Subject to any disclaimer, the term of this patent is extended or adjusted under 35 U.S.C. 154(b) by 527 days.

(21) Appl. No.: 16/286,079

(22) Filed: Feb. 26, 2019

(65) Prior Publication Data
US 2019/0290353 A1   Sep. 26, 2019

Related U.S. Application Data

(60) Provisional application No. 62/645,953, filed on Mar. 21, 2018.

(51) Int. Cl.
*A61B 18/14* (2006.01)
*A61B 18/00* (2006.01)
*A61B 17/29* (2006.01)

(52) U.S. Cl.
CPC .. *A61B 18/1445* (2013.01); *A61B 2017/2903* (2013.01); *A61B 2017/2946* (2013.01); *A61B 2018/0063* (2013.01); *A61B 2018/00946* (2013.01); *A61B 2018/00982* (2013.01); *A61B 2018/1455* (2013.01)

(58) Field of Classification Search
CPC ........ A61B 18/1445; A61B 2017/2903; A61B 2017/2946; A61B 17/2909; A61B 2018/00946; A61B 17/2841; A61B 2017/291
See application file for complete search history.

(56) References Cited

U.S. PATENT DOCUMENTS

| | | |
|---|---|---|
| 702,472 A | 6/1902 | Pignolet |
| 2,801,633 A | 8/1957 | Ehrlich |
| D295,893 S | 5/1988 | Sharkany et al. |
| D298,353 S | 11/1988 | Manno |
| 4,793,218 A | 12/1988 | Jordan et al. |
| 5,100,506 A | 3/1992 | Sturtevant et al. |
| 5,242,456 A | 9/1993 | Nash et al. |
| D343,453 S | 1/1994 | Noda |
| 5,302,234 A | 4/1994 | Grace et al. |

(Continued)

*Primary Examiner* — Thomas A Giuliani
*Assistant Examiner* — Ryan T Clark
(74) *Attorney, Agent, or Firm* — Carter, DeLuca & Farrell LLP (57) ABSTRACT

A surgical instrument includes an end effector and an actuator coupled to the end effector such that actuation of the actuator along a portion of an actuation path manipulates the end effector. A first activation button is electrically coupled to the end effector and is in-line with the actuation path. A first latch component is in-line with the actuation path; a selector is operably coupled to the actuator and movable between a first position and a second position. In the first position, a portion of the selector is positioned to activate the first activation button upon movement of the actuator along a portion of the actuation path to thereby supply energy to the end effector. In the second position, a second latch component of the selector is positioned to engage the first latch component to latch the actuator upon movement of the actuator along a portion of the actuation path.

18 Claims, 6 Drawing Sheets

(56) References Cited

U.S. PATENT DOCUMENTS

| | | |
|---|---|---|
| 5,317,938 A | 6/1994 | de Juan, Jr. et al. |
| D348,930 S | 7/1994 | Olson |
| D349,341 S | 8/1994 | Lichtman et al. |
| D354,564 S | 1/1995 | Medema |
| 5,383,471 A | 1/1995 | Funnell |
| 5,395,364 A | 3/1995 | Anderhub et al. |
| 5,431,667 A | 7/1995 | Thompson et al. |
| 5,486,185 A | 1/1996 | Freitas et al. |
| 5,486,189 A | 1/1996 | Mudry et al. |
| 5,522,830 A | 6/1996 | Aranyi |
| 5,522,839 A | 6/1996 | Pilling |
| 5,539,973 A | 7/1996 | Smith et al. |
| 5,571,129 A | 11/1996 | Porter |
| 5,620,447 A | 4/1997 | Smith et al. |
| 5,626,609 A | 5/1997 | Zvenyatsky et al. |
| D384,413 S | 9/1997 | Zlock et al. |
| 5,707,392 A | 1/1998 | Kortenbach |
| 5,716,374 A | 2/1998 | Francese et al. |
| 5,833,692 A | 11/1998 | Cesarini et al. |
| D408,018 S | 4/1999 | McNaughton |
| 6,013,028 A | 1/2000 | Jho et al. |
| D424,694 S | 5/2000 | Tetzlaff et al. |
| D425,201 S | 5/2000 | Tetzlaff et al. |
| 6,117,158 A | 9/2000 | Measamer et al. |
| 6,202,465 B1 | 3/2001 | Jankoski et al. |
| 6,277,117 B1 | 8/2001 | Tetzlaff et al. |
| D449,886 S | 10/2001 | Tetzlaff et al. |
| H2037 H | 7/2002 | Yates et al. |
| D496,997 S | 10/2004 | Dycus et al. |
| 7,101,371 B2 | 9/2006 | Dycus et al. |
| 7,122,035 B2 | 10/2006 | Canady |
| D533,942 S | 12/2006 | Kerr et al. |
| 7,186,261 B2 | 3/2007 | Prestel |
| D541,938 S | 5/2007 | Kerr et al. |
| 7,267,677 B2 | 9/2007 | Johnson et al. |
| D564,662 S | 3/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,903 S | 6/2010 | Unger et al. |
| D621,503 S | 8/2010 | Otten et al. |
| D627,462 S | 11/2010 | Kingsley |
| D649,643 S | 11/2011 | Allen, IV et al. |
| D661,394 S | 6/2012 | Romero et al. |
| 8,333,765 B2 | 12/2012 | Johnson et al. |
| 8,454,602 B2 | 6/2013 | Kerr et al. |
| 8,523,898 B2 | 9/2013 | Bucciaglia et al. |
| 8,529,566 B2 | 9/2013 | Kappus et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,679,140 B2 | 3/2014 | Butcher |
| 8,685,009 B2 | 4/2014 | Chernov et al. |
| 8,685,056 B2 | 4/2014 | Evans et al. |
| 8,696,667 B2 | 4/2014 | Guerra et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,413 B2 | 6/2014 | Dycus |
| 8,747,434 B2 | 6/2014 | Larson et al. |
| 8,752,264 B2 | 6/2014 | Ackley et al. |
| 8,756,785 B2 | 6/2014 | Allen, IV et al. |
| 8,845,636 B2 | 9/2014 | Allen, IV et al. |
| 8,852,185 B2 | 10/2014 | Twomey |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,900,232 B2 | 12/2014 | Ourada |
| 8,920,461 B2 | 12/2014 | Unger et al. |
| 8,939,972 B2 * | 1/2015 | Twomey ............ A61B 18/1445 606/51 |
| 8,961,513 B2 | 2/2015 | Allen, IV et al. |
| 8,961,514 B2 | 2/2015 | Garrison |
| 8,961,515 B2 | 2/2015 | Twomey et al. |
| 8,968,283 B2 | 3/2015 | Kharin |
| 8,968,298 B2 | 3/2015 | Twomey |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,311 B2 | 3/2015 | Allen, IV et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,492 B2 | 5/2015 | Kerr et al. |
| 9,033,981 B2 | 5/2015 | Olson et al. |
| 9,034,009 B2 | 5/2015 | Twomey et al. |
| 9,039,691 B2 | 5/2015 | Moua et al. |
| 9,039,704 B2 | 5/2015 | Joseph |
| 9,039,732 B2 | 5/2015 | Sims et al. |
| 9,044,243 B2 | 6/2015 | Johnson et al. |
| 9,060,780 B2 | 6/2015 | Twomey et al. |
| 9,072,524 B2 | 7/2015 | Heard et al. |
| 9,113,882 B2 | 8/2015 | Twomey et al. |
| 9,113,899 B2 | 8/2015 | Garrison et al. |
| 9,113,901 B2 | 8/2015 | Allen, IV et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,161,807 B2 | 10/2015 | Garrison |
| 9,192,432 B2 | 11/2015 | Larson et al. |
| 9,259,268 B2 | 2/2016 | Behnke, II et al. |
| 9,265,565 B2 | 2/2016 | Kerr |
| 9,265,568 B2 | 2/2016 | Chernov et al. |
| 9,265,569 B2 | 2/2016 | Hart et al. |
| 9,314,295 B2 | 4/2016 | Garrison |
| 9,375,258 B2 | 6/2016 | Kendrick |
| 9,375,263 B2 | 6/2016 | Allen, IV et al. |
| 9,375,282 B2 | 6/2016 | Nau, Jr. et al. |
| 9,381,059 B2 | 7/2016 | Garrison |
| 9,456,870 B2 | 10/2016 | Chernov et al. |
| 9,486,220 B2 | 11/2016 | Twomey et al. |
| 9,492,221 B2 | 11/2016 | Garrison |
| 9,615,877 B2 | 4/2017 | Tyrrell et al. |
| 9,636,169 B2 | 5/2017 | Allen, IV et al. |
| 9,655,673 B2 * | 5/2017 | McCullough, Jr. ......................... A61B 18/1445 |
| 9,668,806 B2 | 6/2017 | Unger et al. |
| 9,693,816 B2 | 7/2017 | Orszulak |
| 9,713,493 B2 | 7/2017 | Waaler et al. |
| 9,743,976 B2 | 8/2017 | Kendrick |
| 9,820,765 B2 | 11/2017 | Allen, IV et al. |
| 9,844,384 B2 | 12/2017 | Chernov et al. |
| 9,956,030 B2 | 5/2018 | Allen, IV et al. |
| 10,117,705 B2 | 11/2018 | Chernov et al. |
| 10,271,897 B2 | 4/2019 | Allen, IV et al. |
| 2002/0058925 A1 | 5/2002 | Kaplan et al. |
| 2002/0161364 A1 | 10/2002 | Mulier et al. |
| 2004/0148992 A1 | 8/2004 | Huang |
| 2004/0193153 A1 | 9/2004 | Sartor et al. |
| 2005/0090837 A1 | 4/2005 | Sixto et al. |
| 2005/0240218 A1 | 10/2005 | Freed et al. |
| 2006/0052777 A1 | 3/2006 | Dumbauld |
| 2008/0083257 A1 | 4/2008 | Taylor et al. |
| 2008/0264139 A1 | 10/2008 | Rosenbohm et al. |
| 2008/0319467 A1 | 12/2008 | Wenchell |
| 2009/0088743 A1 | 4/2009 | Masuda |
| 2009/0182327 A1 | 7/2009 | Unger |
| 2010/0145334 A1 | 6/2010 | Olson et al. |
| 2011/0144665 A1 | 6/2011 | Malkowski |
| 2012/0239034 A1 | 9/2012 | Horner et al. |
| 2012/0265241 A1 | 10/2012 | Hart et al. |
| 2012/0296238 A1 | 11/2012 | Chernov et al. |
| 2012/0296371 A1 | 11/2012 | Kappus et al. |
| 2012/0303026 A1 | 11/2012 | Dycus et al. |
| 2012/0330308 A1 | 12/2012 | Joseph |

(56) References Cited

U.S. PATENT DOCUMENTS

| | | |
|---|---|---|
| 2013/0022495 A1 | 1/2013 | Allen, IV et al. |
| 2013/0071282 A1 | 3/2013 | Fry |
| 2013/0079774 A1 | 3/2013 | Whitney et al. |
| 2013/0274736 A1 | 10/2013 | Garrison |
| 2013/0304066 A1 | 11/2013 | Kerr et al. |

* cited by examiner

ENERGY-BASED SURGICAL INSTRUMENT HAVING MULTIPLE OPERATIONAL CONFIGURATIONS

CROSS REFERENCE TO RELATED APPLICATION

The present application claims the benefit of and priority to U.S. Provisional Application Ser. No. 62/645,953, filed on Mar. 21, 2018, the entire contents of which are incorporated herein by reference.

BACKGROUND

Technical Field

The present disclosure relates to surgical instruments and, more particularly, to an energy-based surgical instrument having multiple operational configurations.

Background of Related Art

Energy-based surgical instruments such as bipolar electrosurgical forceps are commonly used to treat, e.g., coagulate, cauterize and/or seal, tissue. Such forceps typically include a pair of jaw members that can be manipulated to grasp tissue and apply a mechanical clamping force to the tissue. Electrodes associated with the jaw members are charged to different electrical potentials such that electrosurgical energy may be selectively transferred through the tissue. The combination of electrosurgical energy and mechanical clamping force facilitates treating the tissue.

Some forceps are designed for in-line activation wherein, at the end of the actuation motion required to approximate the jaw members to grasp tissue therebetween, an activation button is activated to initiate the supply of energy to the jaw members. Still other forceps enable latching to maintain the jaw members in an approximated position grasping tissue therebetween. Such forceps may include a separate activation button that is manually activated, e.g., once the jaw members are latched in the approximated position, to initiate the supply of energy to the jaw members. However, these operational configurations are heretofore mutually exclusive, thus requiring a surgeon to choose a device having one or the other.

SUMMARY

The present disclosure provides an energy-based surgical instrument having multiple operational configurations including, in aspects, a first operational configuration wherein the surgical instrument allows in-line activation, and a second operational configuration wherein the surgical instrument is capable of being latched and provides a separate manual activation button. The surgical instrument is readily transitionable between the first and second operations configurations. These and other aspects and features of the present disclosure are detailed below. To the extent consistent, any or all of the aspects and features detailed herein may be used in conjunction with any or all of the other aspects and features detailed herein. Further, as detailed herein and shown in the drawing figures, as is traditional when referring to relative positioning on a surgical instrument, the term "proximal" refers to the end portion of the apparatus or component thereof which is closer to the user and the term "distal" refers to the end portion of the apparatus or component thereof which is further away from the user.

Provided in accordance with aspects of the present disclosure is an energy-based surgical instrument including an end effector assembly, an actuator remote from the end effector assembly and operably coupled thereto such that actuation of the actuator along a portion of an actuation path manipulates the end effector assembly, a first activation button, a first latch component, and a selector. The first activation button is electrically coupled to the end effector assembly, disposed in-line with the actuation path, and is selectively activatable to supply energy to the end effector assembly. The first latch component is disposed in-line with the actuation path. The selector is operably coupled to the actuator and movable between a first position and a second position. In the first position, a portion of the selector is positioned to activate the first activation button upon movement of the actuator along a portion of the actuation path. In the second position, a second latch component of the selector is positioned to engage the first latch component to latch the actuator upon movement of the actuator along a portion of the actuation path.

In an aspect of the present disclosure, movement of the actuator along the actuation path from an un-actuated position to an actuated position manipulates the end effector assembly.

In another aspect of the present disclosure, with the selector disposed in the first position, movement of the actuator along the actuation path from the actuated position to an activated position activates the first activation button.

In another aspect of the present disclosure, with the selector disposed in the second position, movement of the actuator along the actuation path from the actuated position to a latched position engages the first and second latch components to latch the actuator.

In still another aspect of the present disclosure, a second activation button is electrically coupled to the end effector assembly and displaced from the actuation path. The second activation button is selectively activatable to supply energy to the end effector assembly.

In yet another aspect of the present disclosure, the surgical instrument further includes a housing, wherein the actuator is operably coupled to the housing, and a shaft extending distally from the housing, wherein the end effector assembly is disposed at a distal end of the shaft.

In still yet another aspect of the present disclosure, the housing defines a fixed handle portion positioned to oppose the actuator and the first activation button and first latch component are operably coupled to the fixed handle portion of the housing.

In another aspect of the present disclosure, in the latched position, the selector extends into the fixed handle portion wherein the first and second latch components engage on another.

In yet another aspect of the present disclosure, the end effector assembly includes first and second jaw members. In such aspects, manipulation of the end effector assembly includes moving at least one of the first or second jaw members relative to the other from a spaced-apart position to an approximated position.

In still another aspect of the present disclosure, the selector is pivotable relative to the actuator between the first and second positions.

Another energy-based surgical instrument provided in accordance with aspects of the present disclosure includes a housing including a fixed handle portion, a shaft extending distally from the housing, an end effector assembly disposed at a distal end of the shaft, an actuator operably coupled to the end effector assembly and movable relative to the fixed handle portion of the housing along a portion of an actuation path to manipulate the end effector assembly, a first activation button, a first latch component, and a selector. The first activation button is disposed on the fixed handle portion of the housing, electrically coupled to the end effector assembly, disposed in-line with the actuation path, and is selectively activatable to supply energy to the end effector assembly. The first latch component is disposed within the fixed handle portion and in-line with the actuation path. The selector is pivotably coupled to the actuator and movable relative thereto between a first position and a second position. In the first position, a portion of the selector is positioned to activate the first activation button upon movement of the actuator along a portion of the actuation path. In the second position, a second latch component of the selector is positioned to extend into the fixed handle portion of the housing and engage the first latch component to latch the actuator upon movement of the actuator along a portion of the actuation path.

In an aspect of the present disclosure, the actuator includes a movable handle.

In another aspect of the present disclosure, movement of the actuator along the actuation path from an un-actuated position to an actuated position manipulates the end effector assembly.

In still another aspect of the present disclosure, with the selector disposed in the first position, movement of the actuator along the actuation path from the actuated position to an activated position activates the first activation button.

In yet another aspect of the present disclosure, with the selector disposed in the second position, movement of the actuator along the actuation path from the actuated position to a latched position engages the first and second latch components to latch the actuator.

In still yet another aspect of the present disclosure, a second activation button is disposed on the housing, electrically coupled to the end effector assembly, and displaced from the actuation path. The second activation button is selectively activatable to supply energy to the end effector assembly.

In another aspect of the present disclosure, the end effector assembly includes first and second jaw members and wherein manipulation of the end effector assembly includes moving at least one of the first or second jaw members relative to the other from a spaced-apart position to an approximated position.

In another aspect of the present disclosure, when the actuator is latched, the first and second jaw members are latched in the approximated position.

BRIEF DESCRIPTION OF THE DRAWINGS

Aspects and features of the present disclosure are described in detail with reference to the drawing figures wherein like reference numerals identify similar or identical structural elements and.

DETAILED DESCRIPTION

Figure 1:
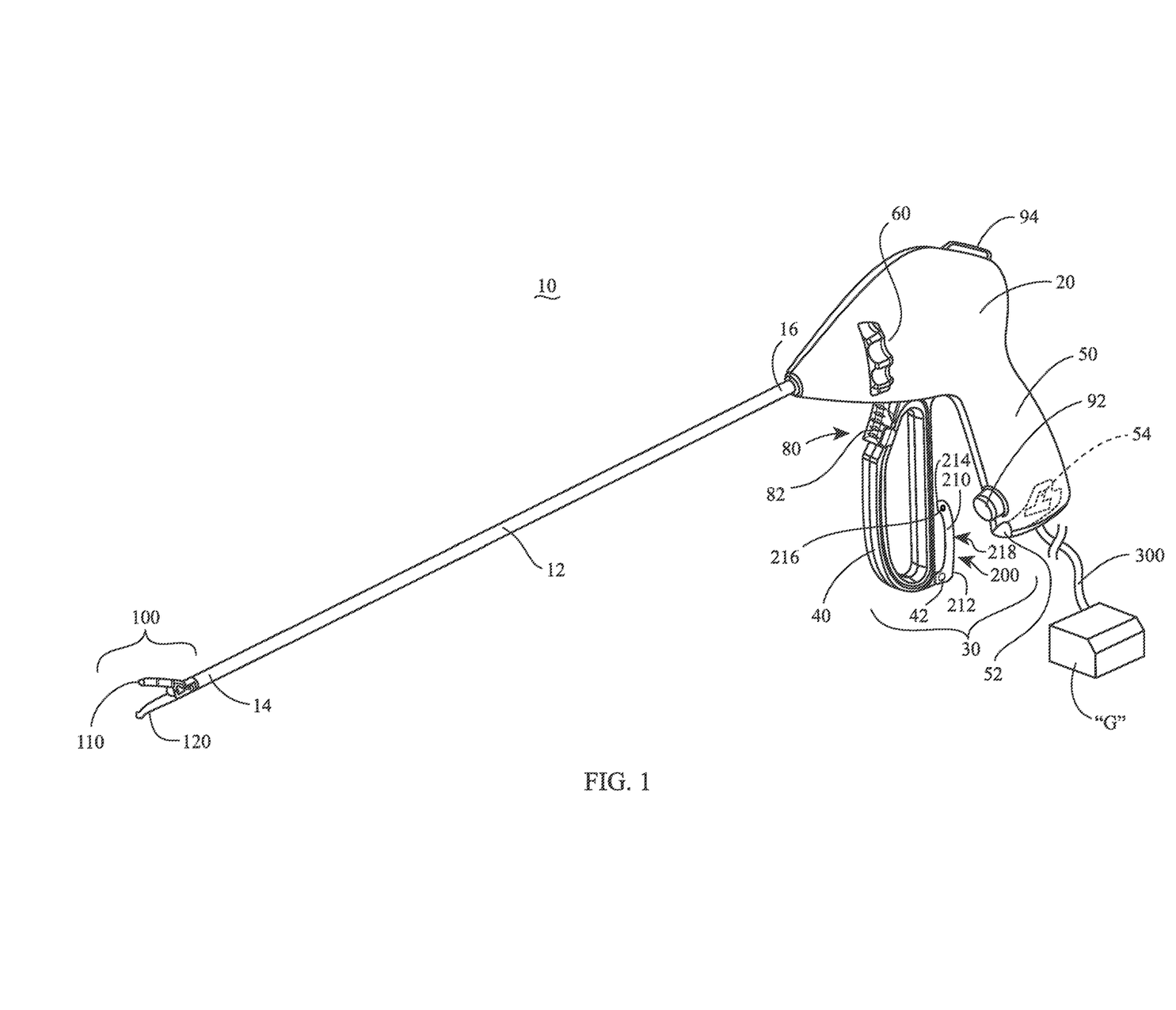
FIG. 1 is a perspective view of an energy-based surgical instrument provided in accordance with the present disclosure.

Referring to FIG. 1, an energy-based surgical instrument 10 is shown configured as a bipolar electrosurgical forceps for use in connection with endoscopic surgical procedures, although instrument 10 may define any suitable configuration for use in endoscopic and/or traditional open surgical procedures. Instrument 10 generally includes a housing 20, a handle assembly 30, a rotating assembly 60, a trigger assembly 80, an end effector assembly 100 including first and second jaw members 110, 120.

Instrument 10 further includes a shaft 12 having a distal end portion 14 configured to engage end effector assembly 100 and a proximal end portion 16 that engages housing 20. Rotating assembly 60 is rotatable in either direction to rotate shaft 12 and end effector assembly 100 relative to housing 20 in either direction. Housing 20 houses the internal working components of instrument 10.

Instrument 10 also includes an electrosurgical cable 300 that connects instrument 10 to an electrosurgical generator "G" or other suitable energy source, although instrument 10 may alternatively be configured as a handheld instrument incorporating energy-generating and power components thereon or therein. Cable 300 includes wires (not shown) extending therethrough, into housing 20, and through shaft 12, to ultimately connect electrosurgical generator "G" to jaw member 110 and/or jaw member 120 of end effector assembly 100. First and second activation buttons 92, 94 disposed on housing 20 are electrically coupled between end effector assembly 100 and cable 300 so as to enable the selective supply of energy to jaw member 110 and/or jaw member 120, e.g., upon activation of either of activation buttons 92, 94. However, other suitable electrical connections and/or configurations for supplying electrosurgical energy to jaw member 110 and/or jaw member 120 may alternatively be provided, as may other suitable forms of energy, e.g., ultrasonic energy, microwave energy, light energy, thermal energy, etc.

Instrument 10 additionally includes a knife assembly 170 operably coupled to trigger assembly 80 and extending through housing 20 and shaft 12. One or both of jaw members 110, 120 defines a knife channel 125 (FIG. 2A) configured to permit reciprocation of a knife blade 172 (FIG. 2A) of knife assembly 170 therethrough, e.g., in response to actuation of trigger 82 of trigger assembly 80. Trigger assembly 80 and knife assembly 170 are described in greater detail, for example, in U.S. Pat. No. 9,655,673, which issued based upon U.S. patent application Ser. No. 14/196,066 filed on Mar. 4, 2014, the entire contents of which is hereby incorporated herein by reference.

Figure 2A:
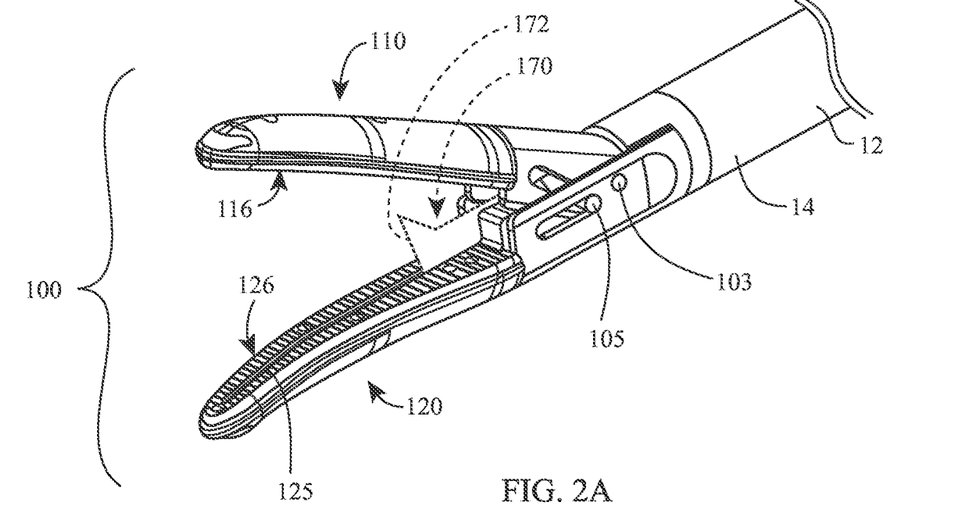
FIG. 2A is an enlarged, perspective view of an end effector assembly of the energy-based surgical instrument of FIG. 1 wherein first and second jaw members of the end effector assembly are disposed in a spaced-apart position.
Figure 2B:
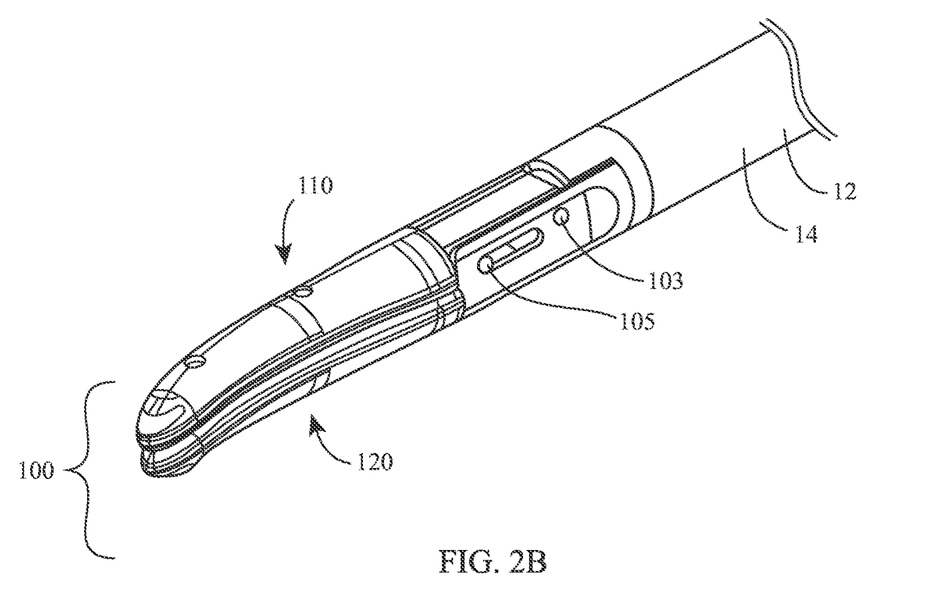
FIG. 2B is an enlarged, perspective view of the end effector assembly of FIG. 2A wherein the first and second jaw members are disposed in an approximated position.

With additional reference to FIGS. 2A and 2B, end effector assembly 100, as noted above, is disposed at distal end portion 14 of shaft 12 and includes a pair of jaw members 110 and 120 pivotable between a spaced-apart position and an approximated position for grasping tissue therebetween. End effector assembly 100 is designed as a unilateral assembly, e.g., wherein one of the jaw members 120 is fixed relative to shaft 12 and the other jaw member 110 is movable relative to both shaft 12 and the fixed jaw member 120. However, end effector assembly 100 may alternatively be configured as a bilateral assembly, e.g., wherein both jaw member 110 and jaw member 120 are movable relative to one another and with respect to shaft 12.

Each jaw member 110, 120 of end effector assembly 100 includes an electrically-conductive tissue-contacting surface 116, 126. Tissue-contacting surfaces 116 are positioned to oppose one another for grasping and treating tissue. More specifically, tissue-contacting surfaces 116, 126 are electrically coupled to the generator "G," e.g., via cable 300, and activation buttons 92, 94 to enable the selective supply of energy thereto for conduction through tissue grasped between jaw members 110, 120, e.g., upon activation of either of activation buttons 92, 94. One or both of tissue-contacting surfaces 116, 126 may include one or more stop members (not shown) extending therefrom to define a minimum gap distance between electrically-conductive tissue-contacting surfaces 116, 126 in the approximated position of jaw members 110, 120, facilitate grasping of tissue, and/or inhibit shorting between electrically-conductive tissue-contacting surfaces 116, 126. The stop member(s) may be formed at least partially from an electrically-insulative material or may be effectively insulative by electrically isolating the stop member(s) from one or both of the electrically-conductive tissue-contacting surfaces 116, 126.

A pivot pin 103 of end effector assembly 100 extends transversely through aligned apertures defined within jaw members 110, 120 and shaft 12 to pivotably couple jaw member 110 to jaw member 120 and shaft 12. A cam pin 105 of end effector assembly 100 extends transversely through cam slots defined within jaw members 110, 120 and is operably engaged with a distal end portion of a drive bar of a drive assembly (not shown) such that longitudinal translation of the drive bar through shaft 12 translates cam pin 105 relative to jaw members 110, 120. More specifically, distal translation of cam pin 105 relative to jaw members 110, 120 urges cam pin 105 distally through the cam slots to thereby pivot jaw members 110, 120 from the spaced-apart position towards the approximated position, although cam slots may alternatively be configured such that proximal translation of cam pin 105 pivots jaw members 110, 120 from the spaced-apart position towards the approximated position. The drive assembly is described in greater detail, for example, in U.S. Pat. No. 9,655,673, previously incorporated herein by reference.

With continued reference to FIGS. 1 and 2A-2B, handle assembly 30 includes a fixed handle 50 and an actuator, e.g., movable handle 40. Fixed handle 50 is integrally associated with housing 20 and movable handle 40 is movable relative to fixed handle 50. Movable handle 40 is ultimately connected to the drive assembly (not shown) that, together, mechanically cooperate to impart movement of jaw members 110 and 120 between the spaced-apart and approximated positions to grasp tissue between electrically-conductive surfaces 116, 126, respectively. More specifically, pivoting of movable handle 40 relative to fixed handle 50 from an un-actuated position towards an actuated position pivots jaw members 110, 120 from the spaced-apart position towards the approximated position. On the other hand, when movable handle 40 is released or returned towards the initial position relative to fixed handle 50, jaw members 110, 120 are returned towards the spaced-apart position. A biasing member (not shown) associated with movable handle 40 and/or the drive assembly may be provided to bias jaw members 110, 120 towards a desired position, e.g., the spaced-apart position or the approximated position.

Referring again to FIG. 1, fixed handle 50 operably supports first activation button 92 thereon in an "in-line" position, wherein first activation button 92 is disposed in the actuation path of movable handle 40, as detailed below. Fixed handle 50 further defines a tunnel 52 providing access to an interior thereof, and a first latch component 54, e.g., a latch track, disposed within the interior of fixed handle 50 and accessible via tunnel 52, as also detailed below. Second activation button 94 is disposed in any suitable position to facilitate manual activation by a user. In embodiments, second activation button 94 may be positioned on housing 20, e.g., as illustrated, to enable the user to hold instrument 10 and activate second activation button 94 with a single hand. In other embodiments, second activation button 94 may be disposed in another position on housing 20, or may be remote therefrom such as, for example, incorporated into a footswitch (not shown).

Figure 4:
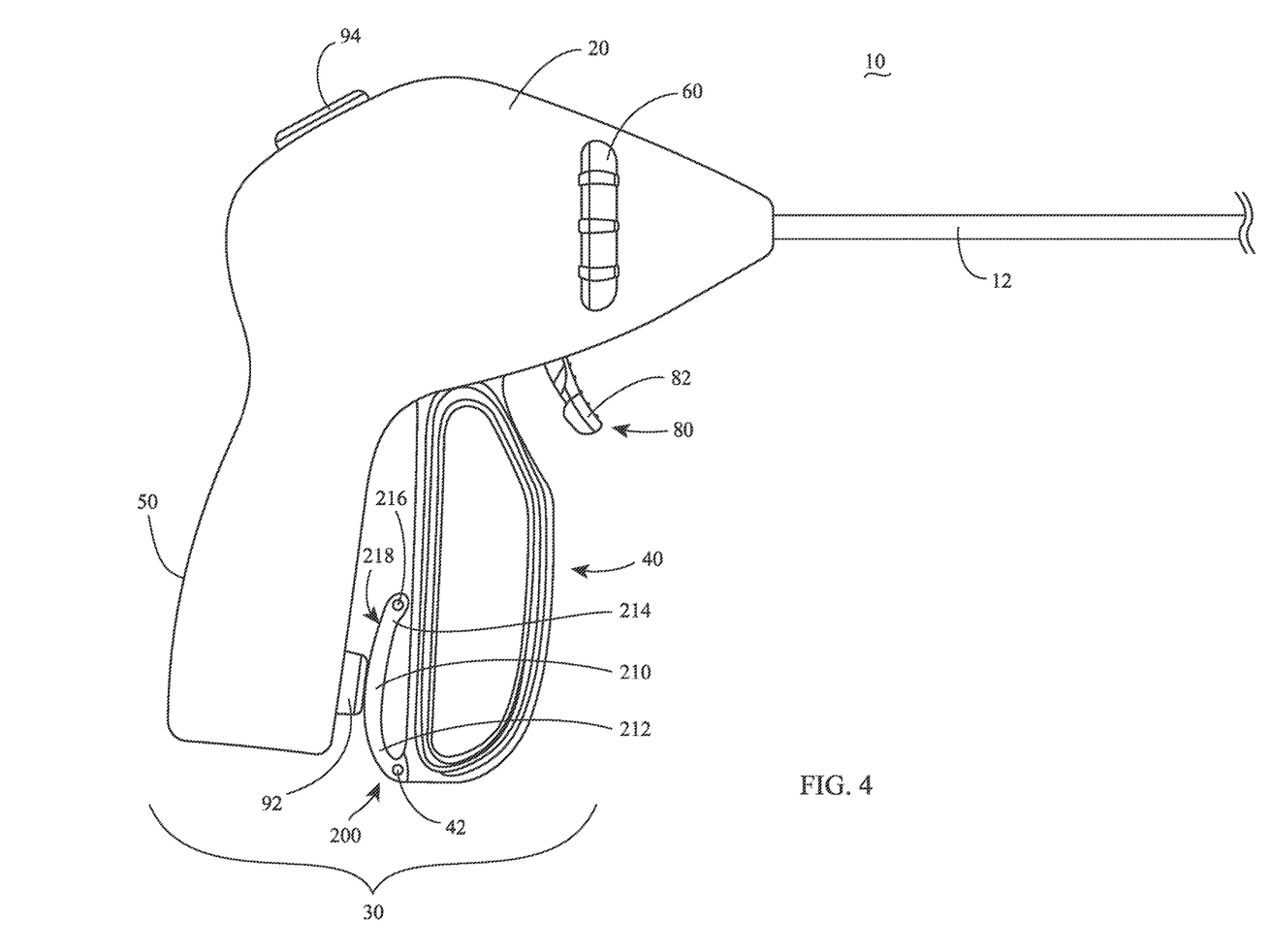
FIG. 4 is a side view of the proximal portion of the energy-based surgical instrument of FIG. 1 disposed in the first configuration with the movable handle disposed in an actuated position.
Figure 5:
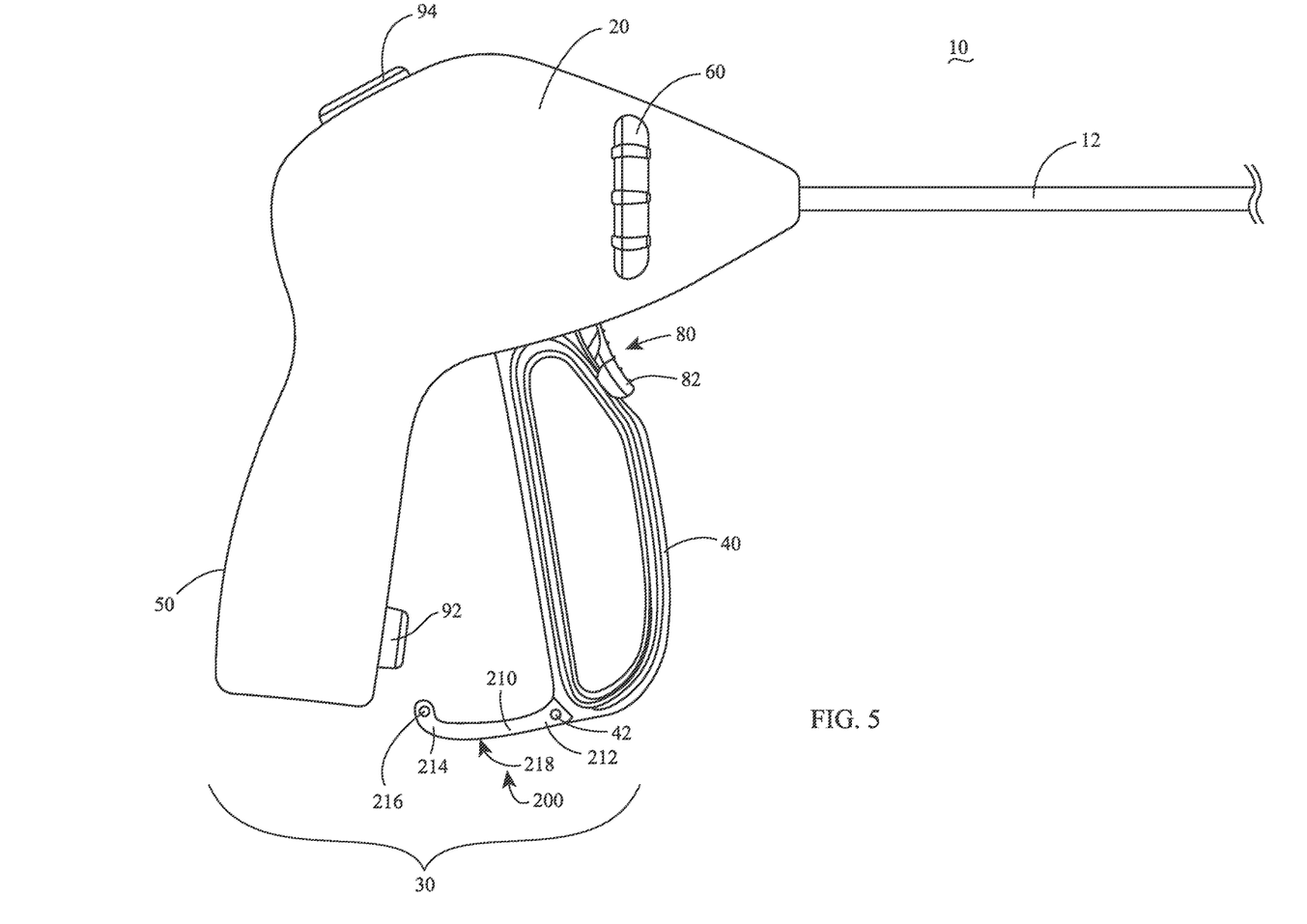
FIG. 5 is a side view of the proximal portion of the energy-based surgical instrument of FIG. 1 disposed in a second configuration with the movable handle disposed in the un-actuated position.
Figure 6:
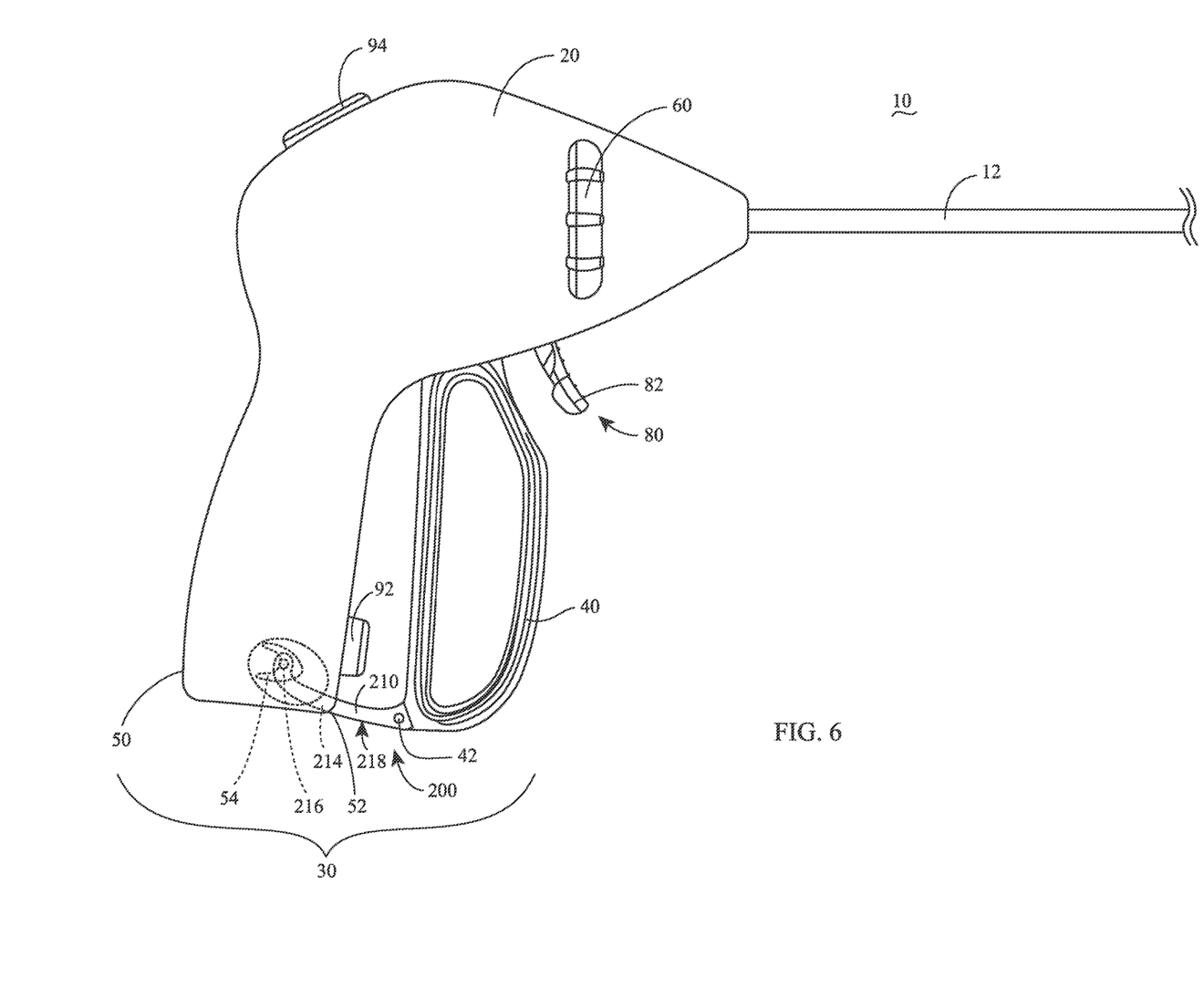
FIG. 6 is a side view of the proximal portion of the energy-based surgical instrument of FIG. 1 disposed in the second configuration with the movable handle latched in the actuated position.

Instrument 10 includes a selector 200 operably associated with movable handle 40 to enable selective transitioning of instrument 10 between a first, in-line activation configuration (FIGS. 3 and 4), and a second, latching, manual activation configuration (FIGS. 5 and 6). Selector 200 includes an arm 210 pivotably coupled to movable handle 40 via a pivot pin 42 towards a first end 212 of arm 210 and extending to a second, free end 214. A second latch component 216, e.g., a latch pin, is disposed towards second, free end 214 of arm 210. Arm 210 further defines an activation surface 218. Selector 200 is movable, e.g., pivotable relative to movable handle 40 about pivot pin 42, between a first position, corresponding to the first, in-line activation configuration (FIGS. 3 and 4), wherein activation surface 218 is operably positioned relative to first activation button 92 to enable activation of first activation button 92 with activation surface 218 upon sufficient actuation of movable handle 40, as detailed below, and a second position, corresponding to the second, latching, manual activation configuration (FIGS. 5 and 6), wherein second latch component 216 is operably positioned relative to tunnel 52 and first latch component 54 to enable passage of second latch component 216 through tunnel 52 and into engagement with first latch component 54 to thereby latch movable handle 40 in the actuated position upon sufficient actuation of movable handle 40, as also detailed below.

The use of instrument 10 in both the first, in-line activation configuration (FIGS. 3 and 4) and the second, latching, manual activation configuration (FIGS. 5 and 6) is described. For use in the first, in-line activation configuration, with reference to FIGS. 1, 3, and 4, arm 210 of selector 200 is moved to the first position such that activation surface 218 is operably positioned relative to first activation button 92. With arm 210 disposed in the first position, and with movable handle 40 disposed in the un-actuated position such that jaw members 110, 120 are disposed in the spaced-apart position, instrument 10 may be manipulated such that tissue to be grasped, treated, and/or divided is disposed between jaw members 110, 120.

Figure 3:
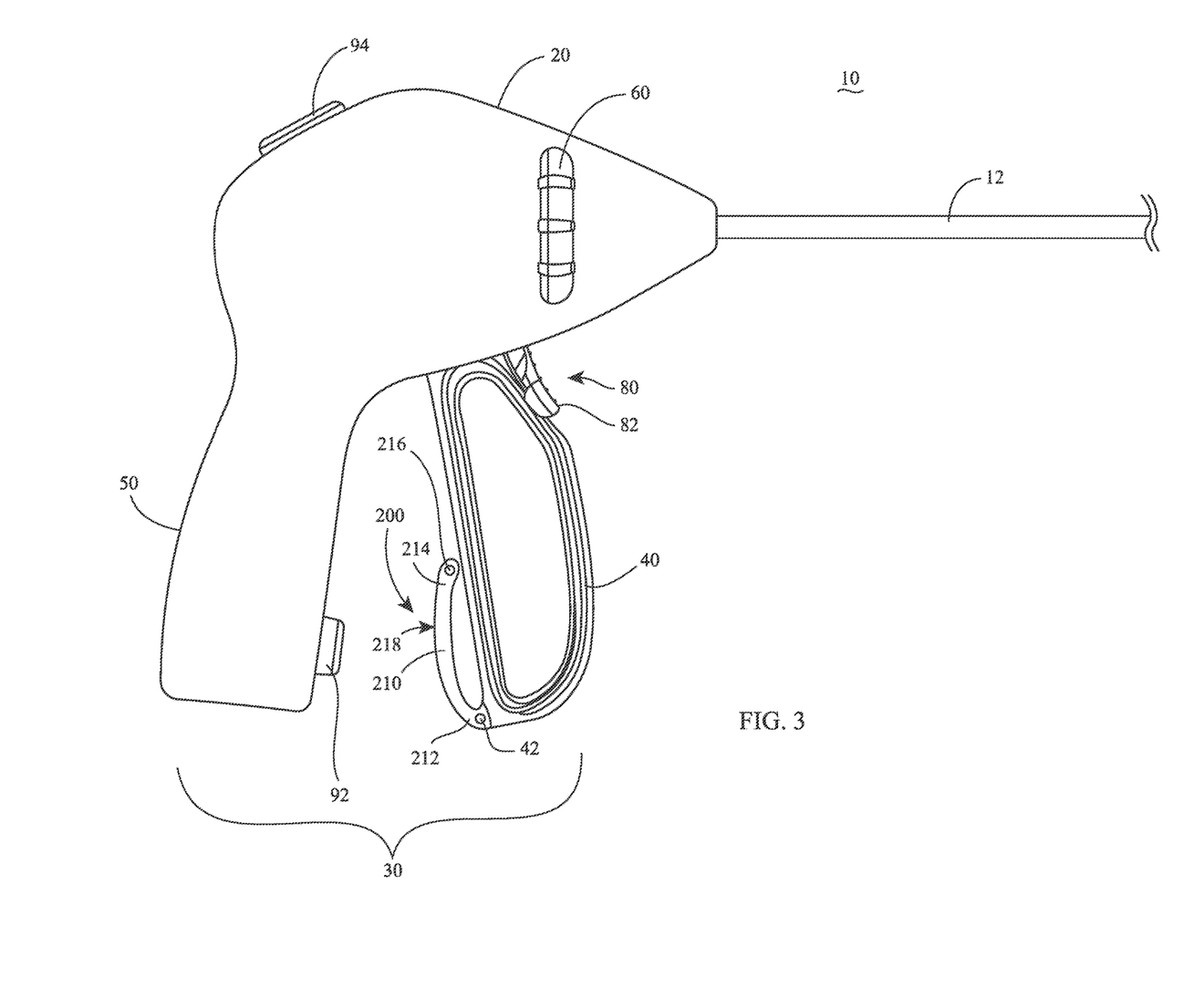
FIG. 3 is a side view of a proximal portion of the energy-based surgical instrument of FIG. 1 disposed in a first configuration with a movable handle of the energy-based surgical instrument disposed in an un-actuated position.

Once tissue to be grasped, treated, and/or divided is disposed between jaw members 110, 120, movable handle 40 is moved from the un-actuated position to the actuated position to pivot jaw members 110, 120 to the approximated position to grasp tissue therebetween. In the actuated position of movable handle 40, activation surface 218 of arm 210 of selector 200 is disposed in close proximity to or in abutment with first activation button 92 but does not activate first activation button 92. Thus, in the actuated position, tissue is mechanically held between jaw members 110, 120 without application of energy thereto.

When it is desired to treat tissue grasped between jaw members 110, 120, movable handle 40 is moved further towards fixed handle 50 from the actuated position to an activated position, wherein, since instrument 10 is disposed in the first, in-line activation configuration, activation surface 218 of arm 210 of selector 200 is urged into first activation button 92 to activate first activation button 92 and initiate the supply of energy from generator "G" (FIG. 1) to jaw members 110, 120 (FIGS. 2A-2B) to treat, e.g., seal, tissue grasped therebetween. More specifically, electrosurgical energy is conducted between tissue-contacting surfaces 116, 126 and through tissue disposed therebetween to treat, e.g., seal, tissue.

After treating tissue, or where it is only desired to cut tissue, trigger 82 of trigger assembly 80 may be actuated to advance knife 172 of knife assembly 170 between jaw members 110, 120 (FIGS. 2A-2B) to cut tissue grasped therebetween.

Once tissue is treated and/or cut as desired, movable handle 40 is released or returned to the un-actuated position such that jaw members 110, 120 are returned to the spaced-apart position, releasing the sealed and/or cut tissue. The above may then be repeated to treat and/or cut other tissue.

Referring to FIGS. 1, 5, and 6, for use of instrument 10 in the second, latching, manual activation configuration, arm 210 of selector 200 is moved to the second position such that second latch component 216 is operably positioned relative to tunnel 52 and first latch component 54.

With arm 210 disposed in the second position, and with movable handle 40 disposed in the un-actuated position such that jaw members 110, 120 are disposed in the spaced-apart position, instrument 10 may be manipulated such that tissue to be grasped, treated, and/or divided is disposed between jaw members 110, 120.

Once tissue to be grasped, treated, and/or divided is disposed between jaw members 110, 120, movable handle 40 is moved from the un-actuated position to the actuated position to pivot jaw members 110, 120 to the approximated position to grasp tissue therebetween. From the actuated position, movable handle 40 may further be moved towards fixed handle 50 to a latched position, wherein second, free end 214 and second latch component 218 of arm 210 extend through (or extends further through) tunnel 52 and into engagement with first latch component 54 such that, upon release of movable handle 40, movable handle 40 is returned to and latched in the actuated position via the engagement of first and second latch components 54, 218, thereby latching jaw members 110, 120 in the approximated position grasping tissue therebetween.

When it is desired to treat tissue grasped between jaw members 110, 120, with jaw members 110, 120 latched in the approximated position, second activation button 94 is manually activated to initiate the supply of energy from generator "G" (FIG. 1) to jaw members 110, 120 (FIGS. 2A-2B) to treat, e.g., seal, tissue grasped therebetween. However, movable handle 40 need not be latched in the approximated position in order to enable application of energy to jaw members 110, 120. Rather, if desired, movable handle 40 may be held in the actuated position (without latching) and second activation button 94 manually activated to initiate the supply of energy from generator "G" (FIG. 1) to jaw members 110, 120 (FIGS. 2A-2B).

After treating tissue, or where it is only desired to cut tissue, trigger 82 of trigger assembly 80 may be actuated to advance knife 172 of knife assembly 170 between jaw members 110, 120 to cut tissue grasped therebetween. Once tissue is treated and/or cut as desired, movable handle 40 is once again moved from the actuated position to the latched position to disengage second latch component 218 from first latch component 54 to enable movable handle 40 to return to the un-actuated position, thereby returning jaw members 110, 120 to the spaced-apart position. The above may then be repeated to treat and/or cut other tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. An energy-based surgical instrument, comprising:
   an end effector assembly;
   an actuator remote from the end effector assembly and operably coupled thereto such that actuation of the actuator along a portion of an actuation path manipulates the end effector assembly;
   a first activation button electrically coupled to the end effector assembly and disposed in-line with the actuation path, the first activation button selectively activatable to supply energy to the end effector assembly;
   a first latch component disposed in-line with the actuation path; and
   a selector operably coupled to the actuator and movable between a first position and a second position, wherein, in the first position, a portion of the selector is positioned to activate the first activation button upon movement of the actuator along a portion of the actuation path and wherein, in the second position, a second latch component of the selector is positioned to engage the first latch component to latch the actuator upon movement of the actuator along a portion of the actuation path.

2. The energy-based surgical instrument according to claim 1, wherein movement of the actuator along the actuation path from an un-actuated position to an actuated position manipulates the end effector assembly.

3. The energy-based surgical instrument according to claim 2, wherein, with the selector disposed in the first position, movement of the actuator along the actuation path from the actuated position to an activated position activates the first activation button.

4. The energy-based surgical instrument according to claim 2, wherein, with the selector disposed in the second position, movement of the actuator along the actuation path from the actuated position to a latched position engages the first and second latch components to latch the actuator.

5. The energy-based surgical instrument according to claim 1, further comprising a second activation button electrically coupled to the end effector assembly and displaced from the actuation path, the second activation button selectively activatable to supply energy to the end effector assembly.

6. The energy-based surgical instrument according to claim 1, further comprising:
 a housing, wherein the actuator is operably coupled to the housing; and
 a shaft extending distally from the housing, wherein the end effector assembly is disposed at a distal end of the shaft.

7. The energy-based surgical instrument according to claim 6, wherein the housing defines a fixed handle portion positioned to oppose the actuator, the first activation button and first latch component operably coupled to the fixed handle portion of the housing.

8. The energy-based surgical instrument according to claim 7, wherein, in the latched position, the selector extends into the fixed handle portion wherein the first and second latch components engage on another.

9. The energy-based surgical instrument according to claim 1, wherein the end effector assembly includes first and second jaw members, and wherein manipulation of the end effector assembly includes moving at least one of the first or second jaw members relative to the other from a spaced-apart position to an approximated position.

10. The energy-based surgical instrument according to claim 1, wherein the selector is pivotable relative to the actuator between the first and second positions.

11. An energy-based surgical instrument, comprising:
 a housing including a fixed handle portion;
 a shaft extending distally from the housing;
 an end effector assembly disposed at a distal end of the shaft;
 an actuator operably coupled to the end effector assembly and movable relative to the fixed handle portion of the housing along a portion of an actuation path to manipulate the end effector assembly;
 a first activation button disposed on the fixed handle portion of the housing, electrically coupled to the end effector assembly, and disposed in-line with the actuation path, the first activation button selectively activatable to supply energy to the end effector assembly;
 a first latch component disposed within the fixed handle portion and in-line with the actuation path; and
 a selector pivotably coupled to the actuator and movable relative thereto between a first position and a second position, wherein, in the first position, a portion of the selector is positioned to activate the first activation button upon movement of the actuator along a portion of the actuation path and wherein, in the second position, a second latch component of the selector is positioned to extend into the fixed handle portion of the housing and engage the first latch component to latch the actuator upon movement of the actuator along a portion of the actuation path.

12. The energy-based surgical instrument according to claim 11, wherein the actuator includes a movable handle.

13. The energy-based surgical instrument according to claim 11, wherein movement of the actuator along the actuation path from an un-actuated position to an actuated position manipulates the end effector assembly.

14. The energy-based surgical instrument according to claim 13, wherein, with the selector disposed in the first position, movement of the actuator along the actuation path from the actuated position to an activated position activates the first activation button.

15. The energy-based surgical instrument according to claim 13, wherein, with the selector disposed in the second position, movement of the actuator along the actuation path from the actuated position to a latched position engages the first and second latch components to latch the actuator.

16. The energy-based surgical instrument according to claim 11, further comprising a second activation button disposed on the housing, electrically coupled to the end effector assembly, and displaced from the actuation path, the second activation button selectively activatable to supply energy to the end effector assembly.

17. The energy-based surgical instrument according to claim 11, wherein the end effector assembly includes first and second jaw members, and wherein manipulation of the end effector assembly includes moving at least one of the first or second jaw members relative to the other from a spaced-apart position to an approximated position.

18. The energy-based surgical instrument according to claim 17, wherein, when the actuator is latched, the first and second jaw members are latched in the approximated position.

* * * * *